(12) United States Patent
Wiedenbein

(10) Patent No.: US 8,337,398 B2
(45) Date of Patent: Dec. 25, 2012

(54) MEDICAL INSTRUMENT

(75) Inventor: Wolfgang Wiedenbein, Seelze (DE)

(73) Assignee: Cardiomedical GmbH, Langenhagen (DE)

( * ) Notice: Subject to any disclaimer, the term of this patent is extended or adjusted under 35 U.S.C. 154(b) by 963 days.

(21) Appl. No.: 11/839,941

(22) Filed: Aug. 16, 2007

(65) Prior Publication Data

US 2008/0064929 A1 Mar. 13, 2008

(30) Foreign Application Priority Data

Sep. 9, 2006 (DE) .................... 10 2006 042 889

(51) Int. Cl.
*A61B 1/04* (2006.01)

(52) U.S. Cl. ........ 600/131; 606/205; 606/208; 606/174; 606/170

(58) Field of Classification Search ............... 604/95.04, 604/103, 106–109, 110–111, 194, 205, 528; 606/51–52, 103, 110–111, 185–186, 205–211, 606/157, 10, 19, 41–46, 250–259, 328–329, 606/139–150, 216–221; 70/58, 77; 128/4, 128/122.1; 16/110.1

See application file for complete search history.

(56) References Cited

U.S. PATENT DOCUMENTS

| | | | | |
|---|---|---|---|---|
| 3,216,754 A * | 11/1965 | Smith et al. | ...................... | 403/51 |
| 5,290,308 A * | 3/1994 | Knight et al. | ................. | 606/205 |
| 5,489,290 A * | 2/1996 | Furnish | .......................... | 606/170 |
| 5,843,122 A * | 12/1998 | Riza | .............................. | 606/207 |
| 5,893,873 A * | 4/1999 | Rader et al. | .................... | 606/205 |
| 6,322,578 B1 * | 11/2001 | Houle et al. | ................... | 606/205 |
| 7,367,743 B2 * | 5/2008 | Bernhardt et al. | ............ | 403/122 |
| 2001/0056286 A1 * | 12/2001 | Etter et al. | ..................... | 606/205 |
| 2004/0249410 A1 * | 12/2004 | Dausch | ......................... | 606/205 |
| 2006/0020288 A1 * | 1/2006 | Leonard | ........................ | 606/205 |
| 2006/0259070 A1 * | 11/2006 | Livneh | .......................... | 606/205 |
| 2007/0112377 A1 * | 5/2007 | Schneiter | ...................... | 606/205 |

FOREIGN PATENT DOCUMENTS

| | | |
|---|---|---|
| DE | 29804860 U1 | 9/1999 |
| DE | 20121753 U1 | 5/2003 |
| DE | 102004025041 A1 | 12/2005 |
| DE | 102004031928 A1 | 1/2006 |
| EP | 0327410 A1 | 8/1989 |
| EP | 0820725 A2 | 1/1998 |

* cited by examiner

*Primary Examiner* — Sam Yao
*Assistant Examiner* — Marie Archer
(74) *Attorney, Agent, or Firm* — Husch Blackwell LLP; H. Frederick Rusche

(57) ABSTRACT

The present invention relates generally to the field of medicine, in particular diagnostics and surgery. By applying endoscopy in the diagnostics and surgery sector, surgical instruments, apparatus or processes are used for examining the interior of living organisms and/or for operative interventions. As such, said invention relates to a medical instrument, in particular a surgical instrument, for use in the endoscopy, comprising a tubular element, work element and an operating element. The operating element advantageously consists of an ergonomic axial grip with an integrated locking mechanism and an instrument shaft cleaning connection.

14 Claims, 3 Drawing Sheets

MEDICAL INSTRUMENT

CROSS-REFERENCE TO RELATED APPLICATIONS

This application claims priority to international application DE 10 2006 042 889.7-35 filed on Sep. 9, 2006.

BACKGROUND OF THE INVENTION

1. Field of the Invention

The present invention generally relates to the field of medicine, in particular to diagnostics and surgery. In the diagnostic and surgery domain surgical instruments, apparatus, or methods are used under the application of endoscopy to examine internal parts of living organisms and/or to perform operative interventions.

2. Related Art

Surgical instruments for endoscopy are sufficiently known. Endoscopic instruments, for instance, also find application in laparoscopic surgery, whereby, with the help of an optical instrument, interventions are undertaken within the abdominal cavity, in particular in minimal invasive surgery. In this case, trocars are introduced into the patient's body through small openings. The endoscopic instruments for imaging and/or flexible gripping devices or cutting tools are finally passed through the openings to facilitate extraction of tissue samples (biopsies). Other surgical instruments also can be inserted in the cavity through the trocar opening. In this manner, for instance, a dorsal or a ventral access to the spinal column can also be created in order to be able to perform a minimal invasive intervention with the help of the surgical instruments. To do this, for instance, just to mention some, a work element, bone curette, pestle, cutting tool, or an exploring tenaculum can be introduced at the distal end of the instrument shaft.

During the operation, whilst the trocar is in place, different endoscopic instruments that carry a special work element find application respectively. To operate the work element located at the distal end of the instruments shaft, the endoscopic instrument contains an operating element at the proximal end of the instruments shaft. The operating element decisively influences the handling of the surgery instrument.

After the operation on the patient, the utilised surgical instruments are contaminated by body fluids and must be cleaned. Most surgical instruments can be dismantled into their unit so components for a cleaning process, during which the internal parts of the tubular instrument shaft pose a big challenge. To dismantle the surgery instrument, the tension and/or compression element is movably guided in the tubular element that is operated at the distal end of a working means and is provided with and is detachable from a coupling element at the proximal end, which is connected with the movable operating element that can be pulled out of the instrument shaft. On the one hand, the coupling point is therefore meant for the transmission of the tension and compression forces from the operating rod of the operating element onto the tension and compression element in the tubular instrument shaft, and on the other hand regarding easy handling, whereby separation of the instrument shaft from the operating element is of special importance.

The invention therefore relates to a medical instrument, in particular a surgical instrument, for to the application in minimal invasive surgery, with a tubular element, work element and an operating element that is detachably located at the proximal end of the tubular element and furthermore with a tension and compression element displaceably guided inside the tubular element, of which the front end operates a work element and the rear end is detachably connected with the movable operating element via a coupling element.

Such medical instruments, in particular surgical instruments, in different designs and embodiments have proven functionality in the endoscopy, in particular in laparoscopy, whereby examinations and minimal invasive application on the patient have multiply proven itself. The operating elements of such surgical instruments are therefore of special importance.

As known from the state of the art, the operating element for surgical instruments of diverse grip designs, for instance the so-called pistol grip, comprise a two-ring grip that is similar to that of a pair of scissors or an axial grip in which the grips are mostly fitted with a locking element.

An example of an operating element with a scissors grip can be derived from DE 20121753 U1. The operating element consists of a grip with two grip parts that move against one another and a detachable latch that locks the grip parts in their respective position, in which the latch features a sliding member attached to one of the grip parts, which is axially slideable in another clamping housing, mounted on the other grip part and that the sliding member, through a spring-loaded clamping element in the clamping housing, can be clamped against sliding and that the clamping element is movable against the spring force from its clamping position.

The embodiment of such an operating element is shown in several operation cases where endoscopic surgery is so large in outer dimensions and too cumbersome and the operating angle, i.e. the position of the angular operating element relative to the instrument shaft is inconvenient in handling. The latch locking element consists of numerous single parts which are likewise relatively large and bulky. Furthermore, the depicted operating element with a connected instrument shaft is not suitable for cleaning the said due to the absence of a flushing connection. The above mentioned details concern the surgical instruments with their gripping parts as disclosed in DE 298 04 860 U1 and DE 697 24 040 T2, in which the grip parts do not contain detachable latches.

For this reason, DE 10 2004 009 200 A1 proposes a surgical instrument for cleaning the instrument shaft, which is formed with a round rod shaft for endoscopic application in pistol-type design with an operating grip for a jaw-type mechanism on the instrument shaft, the operating rod on the grip side is detachable from the rigid shaft rod and designed capable of tilting out for the purpose of cleaning. The disadvantage of this embodiment is that the instrument shaft must is be dismantled for cleaning and coupling in and out of the instrument shaft with the operating element, which is tedious.

Further surgical instruments with a pistol-type grip that find application in the endoscopic surgery are apparent in DE 695 28 416 T2 and DE 10 2004 031 928 A1. Also here the grip parts are not equipped with cleaning connections that facilitate the instrument shaft cleaning. Moreover, locking elements or detachable latches are missing on the movable grips.

The laparoscopy forceps disclosed in DE 10 2004 025 041 A1 is seen as the nearest state of the art for surgery instruments with a pistol-type grip as an operating element. The laparoscopy instrument is connected with a fixed grip with the gripping piece that is movable via a link. On the fixed grip piece is a connection nipple for the connection with a hose for supplying the cleaning medium. The disadvantage of this embodiment is that the operating element is relatively large and does not have a detachable latch for the gripping pieces and that the coupling element is formed out of a plurality of single parts. Likewise, the operating angle, i.e. the position of the angular operating element relative to the instrument shaft has a disadvantageous effect in the handling the surgery instrument in several operating application cases. Furthermore, swiveling the movable branches on the grip part can result in a negative movement of the organ to be operated; this applies to all large handgrip embodiments.

DE 91 14 674.7 is mentioned as a representative of many surgical instruments with axial operating elements or handgrips that do not possess any suitable coupling point for receiving different instrument shafts although they have a detachable latch for handgrips. The instrument cannot be dismantled for cleaning purposes and does not possess a connection on the handgrip, for cleaning liquids.

Another embodiment of a surgical instrument with an axial grip and a locking knob may be derived from EP 0 820 725 B1. This instrument does not contain any coupling point and cannot therefore be dismantled between the instrument shaft and the operating element. A connection for cleaning liquids is also missing on the axial grip.

For the surgical instruments with an axial grip, EP 0 327 410 B1 shows an instrument that is used as a multifunction instrument in the laparoscopy, the possibility of dismantling exists between the shaft and the operating element. Dismantling can occur via a bayonet connection between the cannula and the handgrip, in that a special connection piece is available on the cannula, which features a flushing-line connection. The handgrip is operated electrically for different functions using numerous control means. This special embodiment has different disadvantages. The most significant disadvantage is that the handgrip of the instrument is not compatible with other instrument shafts and the connection of an electrical line on the handgrip makes the handling of the instrument difficult for the surgery.

SUMMARY OF THE INVENTION

The object of the invention is to provide a medical instrument for minimal invasive surgery of the type mentioned at the beginning, thus an instrument that avoids the prior mentioned disadvantages and inadequacies of familiar configurations, and to prescribe a technical solution that enables a cost effective surgical instrument that is equipped with a simple functional geometry for the endoscopy and greater demands. The design of said instrument allows easy coupling in and out of different embodiments of instrument shafts to the coupling point. It is likewise suitable for easier cleaning, and for an integrated and operation-supporting locking mechanism in which the gripping pieces for the operating element are at disposal.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

An exemplary embodiment of the invention is schematically depicted in the drawings and described in detail in the following passage, as follows.

DETAILED DESCRIPTION OF THE PREFERRED EMBODIMENTS

Figure 1:
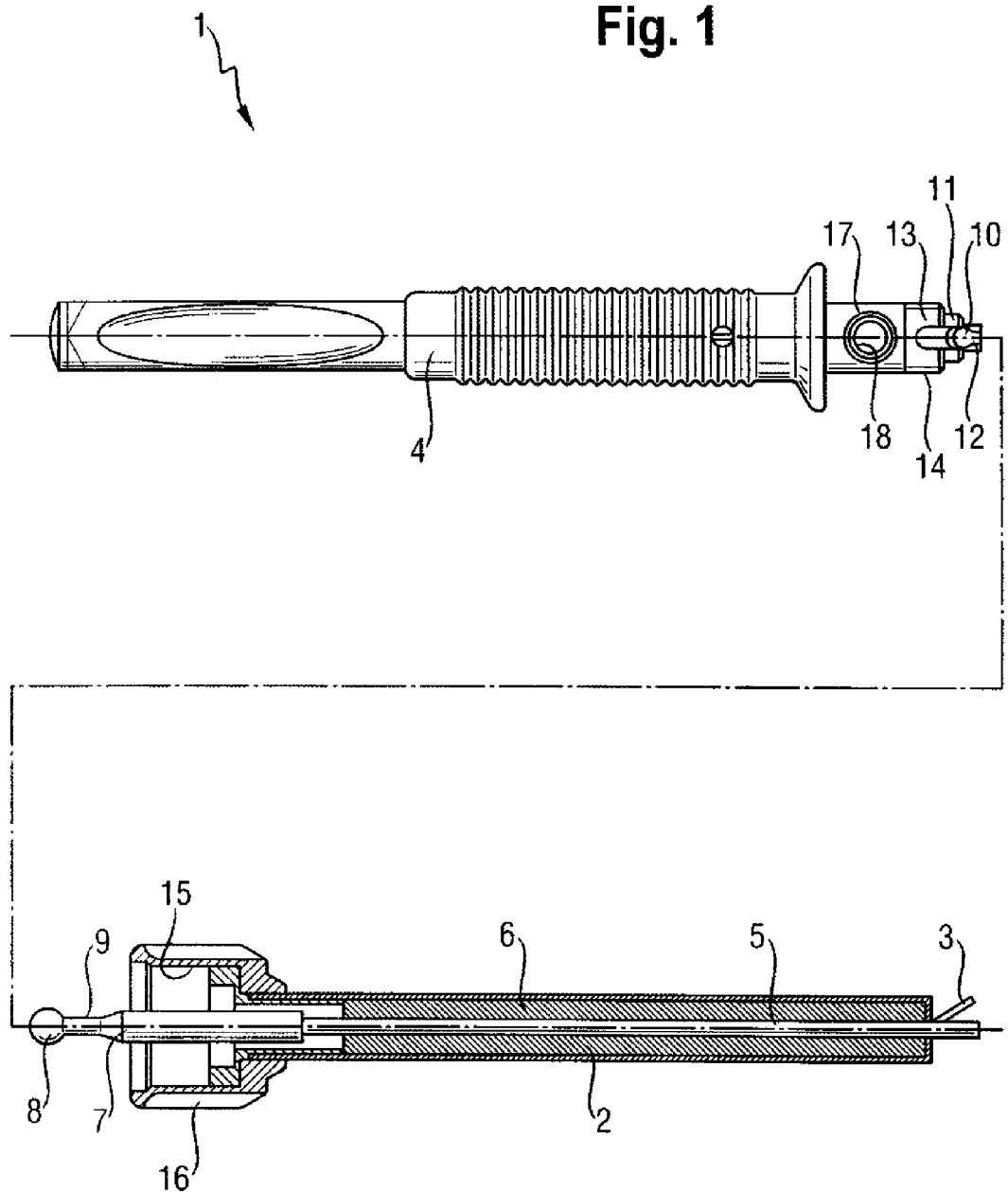
FIG. 1 an overall perspective view of the surgical instrument according to the invention, and FIG. 2 an operating element according to the invention with open grip-position in a side perspective view and FIG. 3 a side view of the operating element in the section with a connected instrument shaft.

The following description of the preferred embodiment(s) is merely exemplary in nature and is in no way intended to limit the invention, its application, or uses.

The surgical instrument 1, depicted in FIG. 1 in plan view, essentially consists of an axial operating element 4, a locking mechanism integrated in it (see FIG. 3), a tubular element 2 located on it (in the section view), hereinafter designated as an instrument shaft, on whose distal end a work element 3 projects. In the drawings, the term "proximal" as in conventional usage is based on the end of the instrument shaft 2, which lies nearer to the operator, while the term "distal" is based on the end farther away from the operator. The work element 3 is located on the front end of the tension and compression element 5. The sliding tension and compression element 5, which is enclosed by the shaft tube 6, guided in the tubular element 2, is provided with a coupling element 7 on the rear end. The coupling element 7 on the tension and compression element 5 consists of a ball 8 that engages in an opening 10 of a coupling 11, which is enclosed in an instrument shaft receptacle 13. Said shaft receptacle 13 is provided with an external thread 14 for fastening of the corresponding inner thread 15, of the union nut 16, located at the proximal end of the instrument shaft 2, whereby said shaft 2 is detachably fastened on the operating element 4. Moreover, on the instrument shaft receptacle 13, a nipple 17 with a bore 18 for accommodating a cleaning line is provided (not depicted). The cleaning line on the connection nipple 17 supplies a medium, such as a flushing liquid or similar medium to the operation point.

Figure 2:
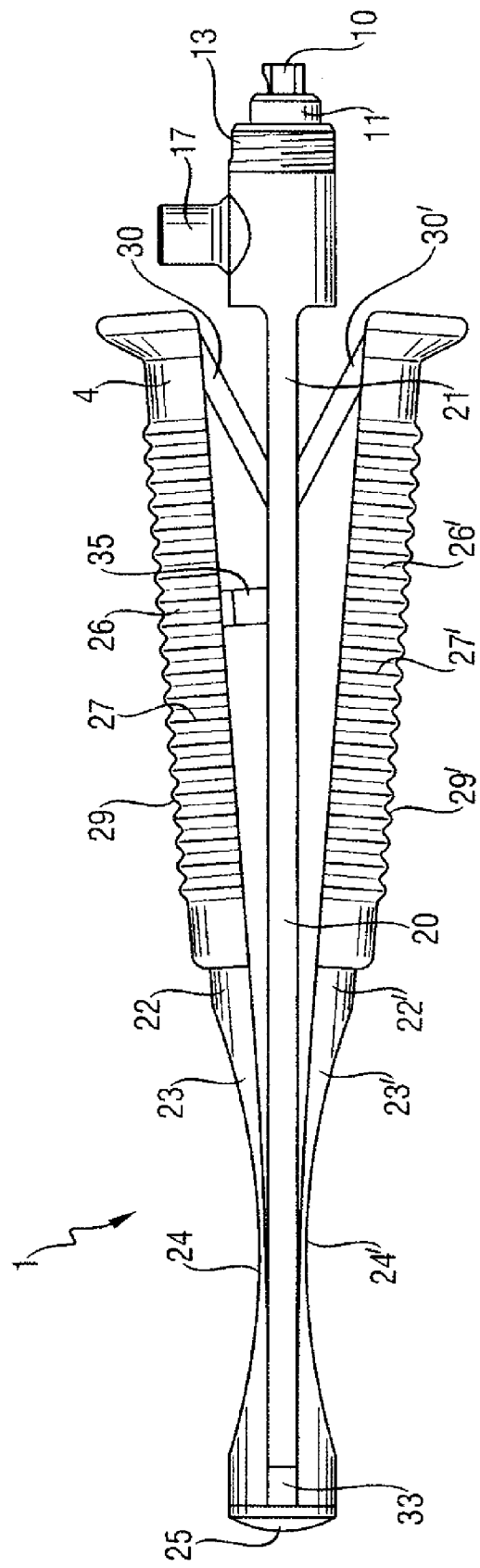
Figure 3:
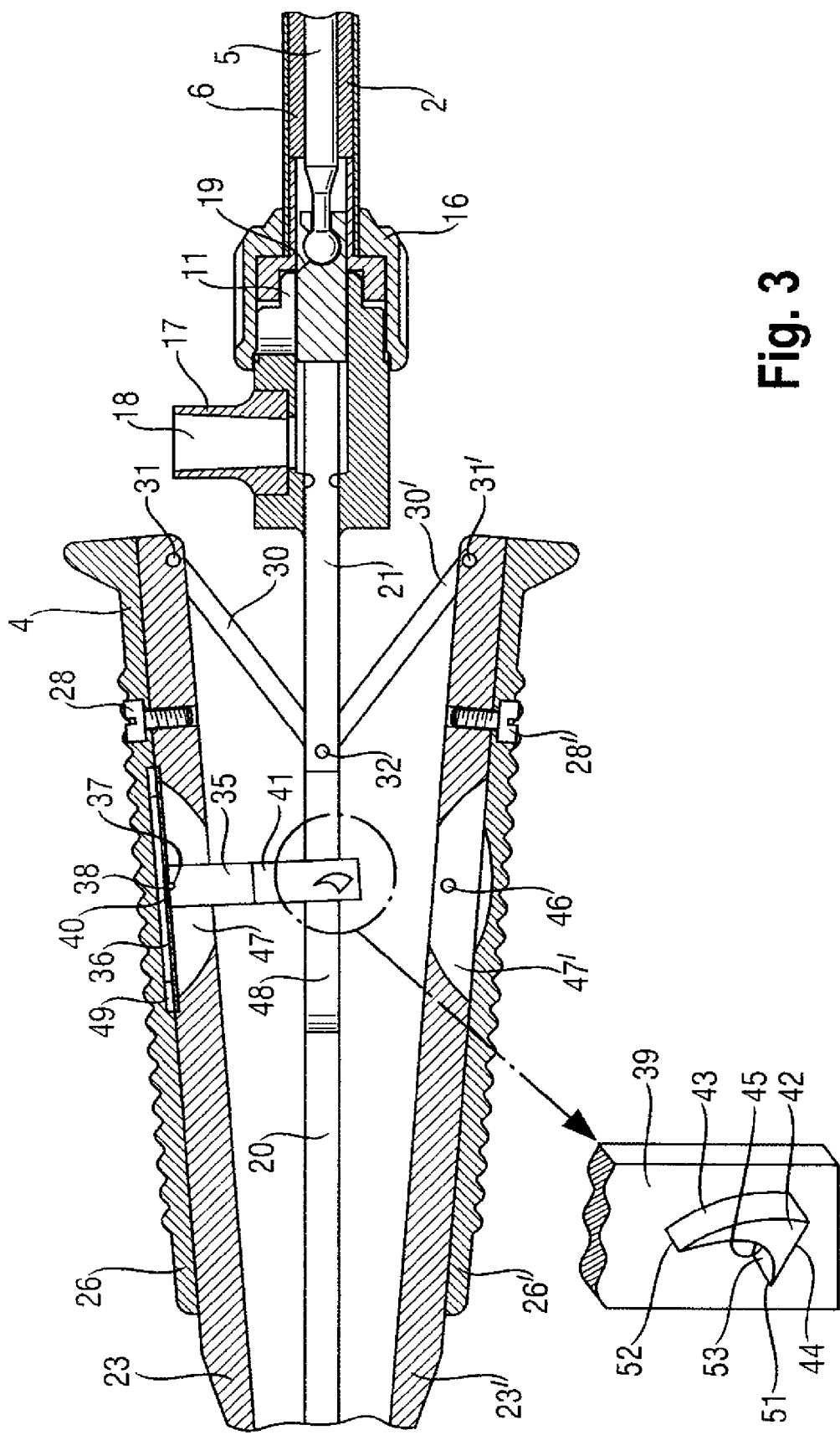

The instrument shaft receptacle 13 is part of the axial operating element 4 explained in detail in its function based on FIG. 2 and FIG. 3 and on the operating rod 21 coupled with movable gripping pieces 27, 27' on the one hand and the coupling with the sliding tension and compression element 5 on the other hand. The function of the integrated locking mechanism 35 is shown in FIG. 3 in connection with the gripping pieces 27, 27' and the base body 20.

An embodiment of the axial operating element 4 according to the invention, with the open position of the two symmetrically located gripping pieces 27, 27' in the side view is shown in FIG. 2 and in the side section view in FIG. 3 in which identical parts are designated with the same reference symbols like in FIG. 1. The axial operating element 4 has the general form of a long stretched cylindrical body without inclination to the axis of the instrument shaft (see FIG. 1), in which the axial operating element 4 consists of a long stretched base body 20, which is mounted movably. The movable base body 20 forms an operating rod 21 at the distal end, which is immersed inside the instrument shaft receptacle 13 and is connected with the coupling 11. The coupling 11 contains an opening 10 for receiving the coupling element 7. The form of the opening 10 of the coupling 11 is designed such that they resemble the form of a key-hole 12, with an insertion slope 19. The key hole 12 with the slope 19 serve for the ease of assembly and disassembly or for receiving the coupling element 7, which is formed by a ball 8 and the constriction of the shaft 9 of the tension and compression element 5, in which the constricted shaft 9 and the ball 8 is similar in the embodiment to the form of vehicle trailer couplings. The coupling 11 therefore establishes a conclusive connection between the operating element 4 and the work element 3.

The movable base body 20 is enclosed by an element 22, which in form and function resembles a pincer. The difference according to the invention is that the pincer arms 23, 23' on the side facing away from the base body 20 feature a constriction 24, 24' made such that a spring-tension occurs in the pincer arms 23, 23', through which they have an opening tendency. The pincer arms 23, 23' form spring-loaded legs. This effect is needed by the locking mechanism 35 according to the invention and is described in detail in FIG. 3. At the proximal end of the base body 20, the apex point 25 of the pincer element 22 is located. The two spring-loaded legs 23, 23' of the pincers element 22 are moreover the carrier of the gripping shells 26, 26' and form with the said the movable gripping pieces 27, 27', which enclose the operating element 4 in a somewhat semi-circular manner. The gripping shells 26', 26' are firmly connected by fastening means 28, 28', such as screws, rivets or adhesive etc. with the spring-loaded legs 23, 23' and are structured on the user surface 29, 29'. The structure corresponds to the ergonomic requirements of a hand, in which the surface structure of the gripping shells 26, 26' in FIG. 2 is formed in a corrugated manner. Other surface structures are likewise possible to manufacture. At the distal end of the movable gripping pieces 27, 27' joint-type components 30, 30' in the form of levers are connected to the bottom side of the spring-loaded legs 23, 23' facing the base housing 20, in which the component 30, 30' on the one hand is pivoted about a fastening pin 31, 31' in the gripping piece 27, 27' and on the other hand about a fastening pin 32 in the base body 20. When closing the symmetrically opposite gripping pieces 27, 27' from the open position of FIG. 2 in the closed position of FIG. 1, the operating rod 21 of the base body 20 is displaced through a linked lever 30, 30' in the axial direction. The displacement of the base body 20 has the effect that the work element 3 connected via the operating rod 21 and the tension and compression element 5, also executes a motion at the end of the distal instrument shaft 2. This motion for instance can entail the closing process of a cutting tool. The displacement of the movable base body 20, which occurs by closing the gripping pieces 27, 27' on the operating element 4, leads towards the proximal end of the operating element 4 and towards the apex point 25 of the pincer element 22. A cavity 33 formed between the apex point 25 and the base body 20 in the open position of the gripping pieces 27, 27'. This cavity 33 when closing the operating element 4 receives the axially sliding base body 20. The gripping pieces 27, 27' are opened from the closed position (FIG. 1) in the open position (FIG. 2), by activating an integrated locking mechanism 35 according to the invention. Detail embodiments of the locking mechanism 35 can be derived from FIG. 3. When opening the gripping pieces 27, 27' nearly no application of force is required by the operator. The force for opening the gripping pieces 27, 27' and sliding the base body 20 in axial direction is introduced according to the invention by the spring force in the spring-loaded legs 23, 23' of the elements 22. A compression spring additionally mounted between the two gripping pieces 27 or between the gripping pieces 27, 27' and the base body 20 is not necessary. The displacement of the movable base body 20 has the effect that the work element 3, connected via the operating rod 21 and the tension and compression element 5, also executes a motion at the end of the distal instrument shaft 2. This motion for instance can entail the opening process of a cutting tool. The displacement of the movable base body 20 which occurs by opening the gripping pieces 27, 27' on the operating element 4, leads towards the distal end of the instrument shaft 2. A cavity 33 occurs between the apex point 25 and the sliding body 20. The deflection of the gripping pieces 27, 27' in the open position is limited by the lever 30.

FIG. 3 shows an opened operating element 4 in lateral illustration in the section with a connected instrument shaft 2 and the locking mechanism 35 according to the invention. The locking mechanism 35 essentially features an interlock spring 36, which is formed as a leaf spring, an interlock arm 39 with an interlock retainer 42 and a fastening pin 37, and a locking pin 46, in which the locking mechanism 35 that is located with its single parts—not visible to the operator—underneath the gripping shells 26, 26' in the recesses 47 of the spring-loaded legs 23, 23' and in the opening 48 of the base body 20. The leaf spring 36, in its geometrical form, corresponds to a flat rectangular body that lies with its bottom side on the surface of the spring-loaded legs 23 in the border area of the recess 47 and thus closes the recess 47, while the top side of the leaf spring 36 engages in a depression 49 located on the bottom side of the gripping shell 26. An the bottom side of the leaf spring 36, an interlock arm 39 is located in this symmetrical middle point, which on the one hand is fastened perpendicularly to the leaf spring 36, with its face surface on said spring, and on the other hand located at the upper end 40, near the face surface and parallel to said surface on a fastening pin 37, in which the fastening pin 37 is spaced in parallel and in transverse direction to the leaf spring 36. The interlock arm 39 is pivoted about the fastening pin 37, in which the elongation of the interlock arm 39 is limited by the size and shape of the recess 47 and the freedom of motion of the leaf spring 36, i.e. the deflection of the interlock arm 39 occurs around the interlock pivot 38, perpendicularly to the leaf spring 36. The interlock arm 39 approximately corresponds to the cross-section of a square column at the top end 40 in its dimensions; at the lower end 41, it contains a constricted step on which an interlock retainer 42 is located. In the open position of the gripping pieces 27, 27' the interlock arm 39 is located, with its respective interlock retainer 42 above the locking pin 46 that is attached to a recess 47' of the spring-loaded legs 23' and is located in the perpendicular position of said part, in which the interlock retainer 42, viewed geometrically from the side, to a great extent corresponds to an acute angled triangle, and as a body of a three-sided prism. One side of the prism has an even surface 44, while the other two sides 43 of the prism are equipped with different radii on the surfaces. The side of the prism facing the locking pin 46 corresponds to the even surface 44 of the prism, which forms an engagement path 44 for the locking pin 46, on whose first surface the locking pin 46 slides along when closing the gripping pieces 27, 27'. The surface of the engagement path 44 is not perpendicular to the locking pin 46, but is inclined under a certain angle relative to the locking pin 44. The angle or the inclination of the engagement path 44 to the locking pin 46 determines the required force that must be exerted when closing the operating element 4 in order to reach the locked or closed position of the gripping pieces 27, 27 (see FIG. 1). When closing the axially provided gripping pieces 27, 27' against the force of the spring-loaded legs 23, 23', the surface of the engagement path 44 knocks the interlock retainer 42 against the solid locking pin 46. In order for the interlock retainer 42 to be able to slide along the locking pin 46, the interlock arm 39 must swing about its interlock pivot 38 and against the perpendicular of the leaf spring 36, until the locking pin 46 reaches the turning point am 51, at which the second adjoining surface 53 of the prism connects to an interlock surface 53 facing inwards and including an interlock position 45. At the turning point I 51 at the end of the engagement path 44, the interlock retainer 42 with the interlock arm 39 is located, in which the maximum deflection and the locking pin 46 stand at the beginning of the second surface 53, in which the turning point 151 is provided with a radius. Since the second surface 53 is designed like an inner radius, the interlock retainer 42 slides due to the spring force generated by the leaf spring 36 up to the interlock position 45 in the interlock surface 53 along the solid locking pin 46. That is, the spring force of the leaf spring 36 tries to return the deflected interlock arm 39 back into its original perpendicular position. If the locking pin 46 is in the interlock position 45, the gripping pieces 27,27' lie on the base body 20 up to a small magnitude and the operating rod 21 is in the pull-back position and the interlock arm 39 of the locking mechanism 35 has approached the perpendicular point of the leaf spring 36 on its circular path. The jointed lever 30, 30' between the gripping piece 27, 27' and the base body 20 are likewise retracted and submerged in the openings (not depicted) of the base body 20. The operating element 4 is closed.

The operating element 4 is opened by pressing the gripping pieces 27, 27', for instance, by means of the index finger and thumb of an operator. By pressing the gripping pieces 27, 27', said pieces will be moved towards one another by a small still-remaining amount, the distance between the gripping pieces 27, 27' and the base body 20 in which at the same time the interlock retainer 42 leaves the interlock position 45 when the locking pin 46 moves towards the second turning point II 52. The interlock retainer 42 thereby slides due to the force generated by the user, while the interlock arm 39 is still deflected out perpendicularly relative to the leaf spring 36, on the second interlock surface, up to the second turning point II 52, along the solid locking pin 46, in which the turning point II 52 is provided with a radius. Once the interlock retainer 42 reaches the turning point II 52, the interlock retainer 42 slides with the third surface 43 due to the leaf spring 36 force, which corresponds to the disengagement path 43, along the locking pin 46, 15 in which the interlock arm swings back to its original perpendicular position. On the disengagement path 43, the interlock arm 39 moves along the circular path, shortly after the turning point II 52, once through the perpendicular position and is deflected to the other side perpendicularly until the disengagement path 44 ends. At the end of the disengagement path 44, the interlock arm 39 swivels through the force of the leaf spring 36 and returns back to its original starting position, and the first surface of the engagement path 44 again stands above the locking pin 46, ready for the next locking process. The locking and unlocking process occurs automatically and supportively to the user in an invisible manner, under the gripping shells 26, 26' or between the gripping pieces 27, 27'. The other opening path of the gripping pieces 27, 27 located on the operating element 4 occurs with the help of the spring force still remaining in the 25 spring-loaded legs 23, 23', until the endpoint is reached. The operating element 4 is opened and the operating rod is positioned forward. The process of closing the operating element 4 and the automatic locking of gripping pieces 27, 27' with the locking mechanism 35 according to the invention can now be repeated.

In order to manufacture a medical instrument with the features of the present invention, in particular a surgical instrument for application in the minimal invasive surgery, the design of a surgical instrument is proposed so that the surgeons have an ergonomic operating element at disposal, which significantly facilitates handling and improves the intervention precision. To achieve this in an optimum manner, it is necessary for the surgeons to initially analyze the intervention to be made on a patient.

During the application of the endoscopic surgery, a trocar—a sharp piercing instrument—is introduced into a body in which the trocar is enclosed inside a cannula. After the trocar has pierced through the body, for instance the abdominal cavity, it is removed whereby the cannula remains inside the body. Frequently, several openings are created by the trocar in the body so that in the one cannula an endoscopic instrument is inserted, in another cannula an observation device and in yet another cannula, fibre optics for lighting the area where surgery work is taking place. However, the possibility of inserting different surgical instruments through one and the same cannula also exists. The operation area tissue can react in a traumatic manner as a result of pushing a surgical instrument in and out.

The endoscopic surgical method comes along with certain problems. Since the active part of the instrument, which is located inside the body, lies far away from the manipulated part of the instrument, outside the body, every slight movement on the manipulated part is magnified when it reaches the active part. That is why the hand of a surgeon must be more secure during the endoscopic intervention than during a similar intervention within the scope of an open surgery. A further difficulty is that the surgeon making the intervention does not directly see the area in which he is operating, but rather views this on a video display, and manipulates the instruments on the basis of what he sees on the video display. Furthermore, the surgeon cannot feel the tissue with his hand to determine its thickness, texture and structure, etc., and the access of surgical instruments is limited. And finally, it is difficult to manipulate the head of the instrument after it is placed inside the cannula. Its movement area is limited. In view of these difficult constraints, the design of the surgical instrument for the endoscopic surgery according to the invention tries to reduce the force necessary to operate the work elements, and to afford the surgeon greater control of the instrument. Because the surgical technology today allows directly controlled access to a variety of internal organs without open surgical interventions, the surgical instruments used during the intervention are of special importance. The access to the operation points can be achieved on the one hand through natural body openings or on the other hand through small incisions with a holding instrument—a trocar—as described above. The possibility of using spreaders or retractors as a holding instrument for the created body entries also exists; the surgical instrument with gripping or cutting means can act through said entries.

For this reason, the first special task of the invention is to provide the surgeon with an ergonomically designed surgical instrument, which essentially facilitates handling and improves the intervention precision. The application of such a surgical instrument according to the invention is conceived for different interventions, in particular, for the application of a retractor, for instance, which is located between the ribs to allow access to the cardia.

A surgical instrument according to the invention, which fulfils the prior mentioned demands, comprises the following elements: a base body, an element with surrounding spring-loaded base-body legs with gripping shells attached to it, at least a component that connects the base body with the spring-loaded legs, in the form of a joint, a locking mechanism that locks and unlocks the two gripping pieces, an instrument shaft receptacle that accommodates the operating base body rod, and features a coupling and a connection nipple. To improve handling and precision of 20 the surgical instrument, the technical locking system design is such that the system independently assumes the functions otherwise performed by the user.

Thereby, the locking mechanism is integrated in the operating element and automatically locks and unlocks the operating element through the motion of the gripping pieces. In that case, the locking mechanism comprises the following elements, an interlock spring, interlock arm, interlock retainer and a locking pin in which the interlock spring, the interlock arm and the interlock retainer form a functional unit. The interlock spring is located between a gripping shell and the spring-loaded leg in which the interlock arm located on the interlock spring features a fastening pin that forms an interlock pivot about which the interlock arm is pivoted. To accommodate the interlock arm, the spring-loaded legs are provided with a recess and the base body with an opening. The interlock arm can therefore swing out to the right and left about the interlock pivot in the recess of the spring-loaded leg and opening in the base body. The swing-out process of the interlock arm occurs through the interlock retainer when it is sliding along the rigid locking pin that is located in the recess of the other spring-loaded leg. The interlock retainer is provided with surfaces along which the locking pin slides. The sliding surfaces of the interlock retainer form an engagement path for the locking pin, an interlock position and a disengagement path in which the locking pin is locked in the locking position of the operating element. In the locked position the gripping pieces are closed on the operating element. That is, the first function of the locking mechanism incorporates locking the operating element automatically when closing the gripping pieces. The locking mechanism only engages when the gripping pieces are pressed together up to the limit stop. The second function comprises the unlocking process. To unlock the operating element, the gripping shells need only a pressing force, generated through the index finger and thumb, whereby, the gripping pieces of the operating element open. The interlocking and disengaging functions occur in that the locking mechanism or the interlock retainer is pushed laterally when the spring-loaded and laterally swiveled interlock arm is pressed against the rigid locking pin by closing the axial handgrip. To lock and unlock, additional hand movements of the user are not necessary, whereby the handling and the precision become more secure during engagement. To determine optimum handling the user interface of the gripping shells are ergonomically designed and structured.

A second special task entails providing an instrument that is easy to clean and sterilise, in regard to the parts that get into direct or indirect contact with organic tissue and body liquids and in order to be able to perform cleaning and sterilisation on the surgical instrument in accordance with the medical requirements of the EU-Guidelines and clean particles from them.

This task is solved according to the invention, in that the operating element is equipped with an instrument shaft receptacle, formed with a nipple to which a flushing line can be connected. The connection nipple according to the invention, located on the instrument shaft, has the advantage that the instrument shaft can be flushed out between different working steps already on the operation table during the operation, whereby the danger of operative contamination or of the inner organs is reduced. The connection nipple is designed in such that different connection possibilities thereon exist. For instance, a line for liquids can be connected in which the liquids can consist of different media, preferably a cleaning liquid. On the operating table, syringes can be used preferably for connection. The connection nipple therefore allows liquid to pass through the instrument shaft. The possibility of the connection nipple to be used for other liquids also exists.

Special importance is accorded to the possibility of dismantling surgical instruments for the purpose of cleaning and sterilisation. The third special task is to provide a surgical instrument that contains an operating element, which on the one hand is suitable for the connection of a plurality of different instrument shafts and thus suitable for different working elements and on the other hand provides a connection point that facilitates quick and easy exchange of instrument shafts. To be able to use surgical instruments according to the invention for different working steps during an operation in a particularly preferred embodiment, the operating element is provided with a detachable instrument shaft. With this, different working elements can be connected with the instrument shaft on the operating element, for instance an exploring tenaculum, dissectors, bone curette, osteotome and pestle, etc., just to mention a few. Whereby, it is not necessary to replace the entire surgical instrument apart from the instrument shaft. The operating element remains the same, which again facilitates the handling. According to the invention, this task is again solved in that the coupling located inside the instrument shaft receptacle features an opening suitable to accommodate instrument shafts which feature a ball-type head as a coupling element. For quick and easy exchange of different instrument shafts or working means provided with a ball head, the opening according to the invention, which resembles a key-hole, is formed with an insertion slope in the coupling. This special feature allows easy assembly and disassembly.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

REFERENCE LIST

| | |
|---|---|
| 1 | Surgical instrument |
| 2 | Tubular element |
| 3 | Work element |
| 4 | Operating element |
| 5 | Tension and compression element |
| 6 | Shaft tube |
| 7 | Coupling element |
| 8 | Ball |
| 9 | Shaft constriction |
| 10 | Opening |
| 11 | Coupling |
| 12 | Key hole |
| 13 | Instrument shaft receptacle |
| 14 | External thread |
| 15 | Internal thread |
| 16 | Union nut |
| 17 | Connection nipple |
| 18 | Bore |
| 19 | Insertion slope |
| 20 | Base body |
| 21 | Operating rod |
| 22 | Element |
| 23, 23' | Pincer arm |
| 24, 24' | Constriction |
| 25 | Apex point |
| 26, 26' | Gripping shells |
| 27, 27' | Gripping pieces |
| 28, 28' | Fastening means |
| 29, 29' | User interface |
| 30, 30' | Components |
| 31, 31' | Fastening pin |
| 32 | Fastening pin |
| 33 | Cavity |
| 34 | |
| 35 | Locking mechanism |

| | |
|---|---|
| 36 | Interlock spring |
| 37 | Fastening pin |
| 38 | Interlock pivot |
| 39 | Interlock arm |
| 40 | Upper end |
| 41 | Lower end |
| 42 | Interlock retainer |
| 43 | Disengagement path |
| 44 | Engagement path |
| 45 | Interlock position |
| 46 | Locking pin |
| 47, 47' | Recess |
| 48 | Opening |
| 49 | Depression |
| 50 | Bottom side |
| 51 | Turning point 1 |
| 52 | Turning point 11 |

What is claimed is:

1. A surgical instrument comprising:
an operating element;
a work element detachably coupled to said operating element;
said operating element having a base body and at least two adjoining gripping shells, each of said gripping shells being connected to said base body by a connecting element;
a locking mechanism to lock and unlock the gripping shells;
said locking mechanism being comprised of one of said gripping shells having an interlock arm pivotally mounted with a retainer having a cam surface;
a spring biasing said interlock arm towards a position substantially perpendicular to said first gripping shell;
an opposing gripping shell having a locking pin;
said interlock arm, cam surface and locking pin being dimensioned to engage in a lock position with a gap being retained between said gripping shells, whereupon squeezing said gripping shells to close said gap is operative to release said pin from said retainer arm, thereby allowing relief from said lock position and spreading of said gripping shells; and
said locking mechanism being comprised of a generally triangular surface having a first substantially straight surface configured to bias said cam surface and said pin towards a locking position, a second curvilinear surface configured to retain said cam surface and pin in a locked position and a third curvilinear surface configured to bias said cam surface and locking pin assembly towards a released position.

2. A surgical instrument, according to claim 1, wherein the locking mechanism is integrated in an operating element.

3. A surgical instrument, according to claim 1 wherein the locking mechanism automatically locks or unlocks an operating element through the motion of the gripping.

4. A surgical instrument, according to claim 1 wherein the locking mechanism comprises an interlock spring, said interlock arm, an interlock retainer and a locking pin.

5. A surgical instrument, according to claim 4 wherein the interlock spring, the interlock arm and the interlock retainer are connected with one another to form a functional unit.

6. A surgical instrument, according to claim 4 wherein the interlock spring is located between a gripping shell and a spring-loaded leg.

7. A surgical instrument, according to claim 6 wherein a swing-out process of the interlock arm occurs by means of the interlock retainer, when said retainer slides along the solid locking pin located in the recess of the spring-loaded leg.

8. A surgical instrument, according to claim 4 wherein the interlock arm is located on the interlock spring and features a fastening pin, about which the interlock arm is pivoted, in which the fastening pin forms an interlock pivot.

9. A surgical instrument, according to claim 8 wherein the interlock arm can swing out to the right and left about the interlock pivot in the recess of the spring-loaded leg and the opening in the base body.

10. A surgical instrument, according to claim 1 wherein the spring-loaded leg features a recess and the base body features an opening.

11. A surgical instrument, according to claim 1 wherein the gripping shells are ergonomically designed and structured on the user interface surface.

12. The surgical instrument of claim 1 wherein a second squeezing of said gripping shells to close said gap is operative to re-lock the instrument in said locked position.

13. The surgical instrument of claim 12 wherein said gripping shells are biased towards an open position of said gripping shells.

14. The surgical instrument of claim 1 wherein said cam surface is further comprised of a generally closed triangular surface having three outside surfaces comprising said first substantially straight surface configured to bias said cam surface and said pin towards a locking position, said second curvilinear surface configured to retain said cam surface and pin in a locked position and said third curvilinear surface configured to bias said cam surface and locking pin assembly towards a released position.

* * * * *